United States Patent
Stack

(10) Patent No.: US 9,187,411 B2
(45) Date of Patent: Nov. 17, 2015

(54) LEUKOTRIENE B₄ ANTAGONIST COMPOUND

(71) Applicant: Eli Lilly and Company, Indianapolis, IN (US)

(72) Inventor: Douglas Richard Stack, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 30 days.

(21) Appl. No.: 14/359,924

(22) PCT Filed: Jan. 4, 2013

(86) PCT No.: PCT/US2013/020195
§ 371 (c)(1),
(2) Date: May 22, 2014

(87) PCT Pub. No.: WO2013/106238
PCT Pub. Date: Jul. 18, 2013

(65) Prior Publication Data
US 2014/0343151 A1 Nov. 20, 2014

Related U.S. Application Data

(60) Provisional application No. 61/584,975, filed on Jan. 10, 2012, provisional application No. 61/585,799, filed on Jan. 12, 2012.

(51) Int. Cl.
*C07C 233/25* (2006.01)
(52) U.S. Cl.
CPC .................. *C07C 233/25* (2013.01)
(58) Field of Classification Search
CPC .................................................. C07C 233/25
USPC ........................................ 514/563; 562/455
See application file for complete search history.

(56) References Cited

U.S. PATENT DOCUMENTS 5,462,954 A 10/1995 Baker et al.

FOREIGN PATENT DOCUMENTS

| WO | WO 96/36347 A1 | 11/1996 |
| WO | WO 98/42346 A1 | 10/1998 |
| WO | WO 01/34135 A2 | 5/2001 |
| WO | WO 01/34198 A2 | 5/2001 |
| WO | WO 01/85166 A1 | 11/2001 |

OTHER PUBLICATIONS

Sawyer, et al., "Synthetic and Structure/Activity Studies on Acid-Substituted 2-Arylphenols: Discovery of 2-[2-Propyl-3-[3-2-ethyl-4-(4-fluorophenyl)-5-hydroxyphenoxy]-propoxy]phenoxy] benzoic Acid, a High-Affinity Leukotriene B4 Receptor Antagonist1," J. Med. Chem., 38, pp. 4411-4432 (1995).

Zhao, et al., "The 5-lipoxygenase pathway promotes pathogenesis of hyperlipidemia-dependent aortic aneurysm," Nature Medicine, 10(9), pp. 966-973 (Aug. 2004).

Whatling, et al., "The potential link between atherosclerosis and the 5-lipoxygenase pathway: investigational agents with new implications for the cardiovascular field," Expert Opinion, 16(12), pp. 1879-1893 (2007).

Hicks, et al., "Leukotriene B4 receptor antagonists as therapeutics for inflammatory disease: preclinical and clinical developments," Expert Opinion, 16(12), pp. 1909-1920 (2007).

Kristo, et al., "Pharmacological inhibition of BLT1 diminishes early abdominal aneurysm formation," Atherosclerosis, 210, pp. 107-113 (2010).

Ahluwalia, et al., "Inhibited Aortic Aneurysm Formation in BLT1-Deficient Mice," The Journal of Immunology, 179, pp. 691-697 (2007).

Nanda, et al., "Molecular Targets and Abdominal Aortic Aneurysms," Recent Patents on Cardiovascular Drug Discovery, 4, pp. 150-159 (2009).

Poeckel & Funk, "The 5-lipoxygenase/leukotriene pathway in preclinical models of cardiovascular disease," Cardiovascular Research, 86, pp. 243-253 (2010).

Cao, et al., "Angiotensin II-induced abdominal aortic aneurysm occurs independently of the 5-lipoxygenase pathway in apolipoprotein E-deficient mice," Prostaglandins Other Lipid Mediat., 84(1-2), pp. 34-42 (Aug. 2007).

Michael, et al., "BLT1 Receptor Antagonist LY1 Reduces Murine Atherosclerosis and Abdominal Aortic Aneurysms ," accessed Dec. 8, 2011.

(Continued)

*Primary Examiner* — Fereydoun G Sajjadi
*Assistant Examiner* — Amy C Bonaparte
(74) *Attorney, Agent, or Firm* — John C. Demeter

(57) ABSTRACT

The present invention provides a compound of Formula (I): or a pharmaceutically acceptable salt thereof. Also, the present invention provides a pharmaceutical composition comprising a compound of Formula (I) or a pharmaceutically acceptable salt thereof and a pharmaceutically acceptable carrier. The present invention further provides methods for treating abdominal aortic aneurysm or atherosclerosis comprising administering a therapeutically effective amount of a compound of Formula (I) or a pharmaceutically acceptable salt thereof or a pharmaceutical composition comprising a pharmaceutically acceptable carrier and a therapeutically effective amount of a compound of Formula (I) or pharmaceutically acceptable salt thereof.

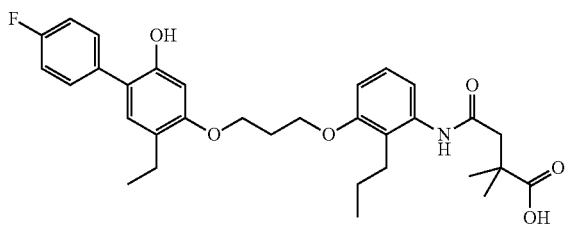

3 Claims, No Drawings

(56) References Cited

OTHER PUBLICATIONS

Back, "Inflammatory Signaling Through Leukotriene Receptors in Atherosclerosis," Current Atherosclerosis Reports, 10, pp. 244-251 (2008).

Aiello, et al., "Leukotriene B4 Receptor Antagonism Reduces Monocytic Foam Cells in Mice," Arteriosclerosis, Thrombosis, and Vascular Biology, 22, pp. 443-449 (2002).

Rosenfeld, "Leukocyte recruitment into developing atherosclerotic lesions: the complex interaction between multiple molecules keeps getting more complex," Arteriosclerosis, Thrombosis, and Vascular Biology, 22, pp. 361-363 (2002).

Spanbroek, et al., "Expanding expression of the 5-lipoxygenase pathway within the arterial wall during human atherogenesis," PNAS, 100(3), pp. 1238-1243 (2003).

Ross, "Atherosclerosis—an inflammatory disease," New England Journal of Medicine, 340(2), pp. 115-126 (1999).

Thompson, "Abdominal Aortic Aneurysms: Basic Mechanisms and Clinical Implications," Current Problems in Surgery, 39(2), pp. 110-230 (Feb. 2002).

Houard, et al., "Differential inflammatory activity across human abdominal aortic aneurysms reveals neutrophil-derived leukotriene B4 as a major chemotactic factor released from the intraluminal thrombus," FASEB, 23(5), pp. 1376-1383 (May 2009).

SEQUENCE LISTING

```
<160> NUMBER OF SEQ ID NOS: 1

<210> SEQ ID NO 1
<211> LENGTH: 32
<212> TYPE: DNA
<213> ORGANISM: Artificial Sequence
<220> FEATURE:
<223> OTHER INFORMATION: synthetic construct

<400> SEQUENCE: 1
taatgtaggt aatagttcaa taggtcaaag gg                                    32
```

LEUKOTRIENE B₄ ANTAGONIST COMPOUND

This application is a national phase application under 35 U.S.C. §371 for PCT/US2013/020195, filed Jan. 4, 2013, which claims the benefit under 35 U.S.C. Section 119 of U.S. Provisional Patent Application 61/584,975, filed Jan. 10, 2012, and U.S. Provisional Application 61/585,799, filed Jan. 12, 2012.

Leukotriene $B_4$ ($LTB_4$) is an eicosanoid proinflammatory lipid mediator generated by a pathway downstream of the enzymes 5-lipoxygenase and leukotriene $A_4$ hydrolase. $LTB_4$ activates multiple leukocyte subsets leading to cell recruitment, production of reactive oxygen species, and induction of gene expression. $LTB_4$ signals primarily through its high-affinity G protein-coupled receptor, BLT1, and, to a lesser extent, its low-affinity $BLT_2$ receptor. The $BLT_1$ receptor is highly expressed in specific subsets of circulating peripheral blood leukocytes, as well as on nonleukocytes including endothelial cells and smooth muscle cells. $LTB_4$ is involved in the vascular pathology of several inflammatory conditions including abdominal aortic aneurysm (AAA) and atherosclerosis.

A degenerative disorder, AAA is characterized by continuous progression of inflammation of the aortic wall, uncontrolled local production of destructive proteases, destruction of structural proteins, and depletion of medial smooth muscle cells. The early or acute phase begins with recruitment of inflammatory cells. Injury results when local reactive oxygen, leukotrienes, chemokines and matrix degradation products act in concert to activate various protease systems. The extracellular matrix of the abdominal aorta may also be weakened by the excess degradation leading to a condition known as AAA.

The role of lipid deposition in the formation of atherosclerotic plaque in the intima of arteries is well established. Another major factor in atherogenesis is inflammatory cell recruitment to intimal lesions. Plaques that have both a high lipid and inflammatory cell content are vulnerable to rupture and subsequent events including myocardial infarction and cereberal ischemia.

Currently, AAA is the tenth leading cause of death in men greater than 55 years old. There is no known approved pharmaceutical treatment indicated for AAA. Also, despite the availability of pharmaceutical treatments that deal with high cholesterol levels and high blood pressure, atherosclerosis remains an area of further medical need. Further, despite the promise of leukotriene antagonists such as those in U.S. Pat. No. 5,462,954 and WO 98/42346, no $LTB_4$ antagonist has been approved for inflammatory indications. $LTB_4$ antagonist compounds have been shown to also be ligands of peroxisome proliferator activated receptors (PPAR) which is believed to limit their development as anti-inflammatory agents. Antagonism of $LTB_4$, with no meaningful PPAR binding, provides an option for addressing the medical needs for treating AAA, atherosclerosis, or both.

The present invention provides a compound of Formula (I):

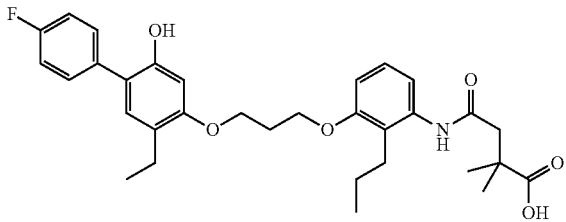 [SMILES: CCCc1c(NC(=O)CC(C)(C)C(=O)O)cccc1OCCCOc1cc(O)c(-c2ccc(F)cc2)cc1CC]

or a pharmaceutically acceptable salt thereof. The compound of formula (I) is named, 4-[[3-[3-[2-Ethyl-4-(4-fluorophenyl)-5-hydroxy-phenoxy]propoxy]-2-propyl-phenyl]amino]-2,2-dimethyl-4-oxo-butanoic acid according to the IUPAC naming feature in Symyx® Draw version 3.2.NET.

A second aspect of the present invention provides a sodium salt of a compound of Formula 1 which is Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate.

A third aspect of the present invention provides a pharmaceutical composition comprising a compound of Formula (I) or a pharmaceutically acceptable salt thereof and a pharmaceutically acceptable carrier.

A fourth aspect of the present invention provides a pharmaceutical composition comprising Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate and a pharmaceutically acceptable carrier.

A fifth aspect of the present invention provides a method for treating AAA, atherosclerosis, or both in a patient in need thereof, comprising administering a therapeutically effective amount of a compound of Formula (I), or a pharmaceutically acceptable salt thereof, or a pharmaceutical composition comprising a pharmaceutically acceptable carrier and a therapeutically effective amount of a compound of Formula (I), or a pharmaceutically acceptable salt thereof, to said patient.

A sixth aspect of the present invention provides a method for treating AAA, atherosclerosis, or both in a patient in need thereof, comprising administering a therapeutically effective amount of a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate or a pharmaceutical composition comprising a pharmaceutically acceptable carrier and a therapeutically effective amount of a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate to said patient.

A seventh aspect of the present invention provides a compound of Formula (I) or a pharmaceutically acceptable salt thereof, for use in therapy.

An eighth aspect of the present invention provides a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate for use in therapy.

A ninth aspect of the present invention provides a compound of Formula (I), or a pharmaceutically acceptable salt thereof, for use in the treatment of AAA, atherosclerosis, or both.

A tenth aspect of the present invention provides a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate for use in the treatment of AAA, atherosclerosis, or both.

An eleventh aspect of the present invention is the use of a compound of Formula (I), or a pharmaceutically acceptable salt thereof, for the manufacture of a medicament for the treatment of AAA, atherosclerosis, or both.

A twelfth aspect of the present invention is the use of a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate for the manufacture of a medicament for the treatment of AAA, atherosclerosis, or both.

Another aspect of the present invention provides a pharmaceutical composition comprising a compound of Formula (I), or pharmaceutically acceptable salt thereof, in combination with a pharmaceutically acceptable carrier, and optionally one or more other therapeutic agents.

A further aspect of the present invention provides a pharmaceutical composition comprising a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate in combination with a pharmaceutically acceptable carrier, and optionally one or more other therapeutic agents.

Yet another aspect of the present invention provides a compound of Formula (I), or a pharmaceutically acceptable salt thereof, for use in the treatment of AAA, or atherosclerosis, or both.

A further aspect of the present invention provides a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate for use in the treatment of AAA or atherosclerosis, or both.

Yet another aspect of the present invention provides the use of a compound of Formula (I), or a pharmaceutically acceptable salt thereof, for the manufacture of a medicament for the treatment of AAA or atherosclerosis, or both.

A still further aspect of the present invention provides the use of a compound Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate for the manufacture of a medicament for the treatment of AAA or atherosclerosis, or both.

As used above and throughout the specification of the invention, the following terms, unless otherwise indicated will have the following meaning:

The term "abdominal aortic aneurysm" (or "AAA") as used herein shall mean a localized dilation or bulge of the abdominal aorta, generally understood to be that portion of the aorta below the diaphragm, in a mammal causing the size of at least a segment of the abdominal aorta to exceed the size of an otherwise considered normal state of 2 cm. The abdominal aorta may be measured and compared in terms of any measurement dimension including but not limited to outer diameter, luminal diameter, luminal perimeter, and luminal area. The means for measurement and diagnosis may be through the use of ultrasound, CT scan, or other imaging techniques. For example, AAA is present in a human when the outer aortic diameter is greater than 3 cm. If the outer aortic diameter is however more than 5 cm, then immediate surgical or endovascular repair (stent or graft) is the standard of care to prevent rupture and potential fatality. If however such treatment is unavailable or not an option due to any reason, e.g., age, then this population may also be treated using the present invention.

The term "atherosclerosis" as used herein shall mean a lipid-rich plaque or lesion in the intima of arteries.

The term "in need thereof" as used herein shall mean having or being diagnosed with a condition, AAA or atherosclerosis, that requires treatment.

The term "patient" as used herein shall mean a mammal such as a dog, cat, horse, cow, sheep, pig, or human.

The term "pharmaceutically acceptable salt thereof" refers to salts of the compounds of the present invention. Examples and methods for their preparation are well within the knowledge of those skilled in the art. See, for example, Stahl et al., "Handbook of Pharmaceutical Salts: Properties, Selection and Use," VCHA/Wiley-VCH, 2002; and S. M. Berge, et al., "Pharmaceutical Salts," *Journal of Pharmaceutical Sciences*, Vol. 66, No. 1, January 1977, pages 1-19. Particular pharmaceutically acceptable salts include sodium, potassium, calcium and magnesium. A preferred pharmaceutically acceptable salt of the present invention is sodium.

The term "therapeutically effective amount" refers to the amount or dose of a compound of Formula (I), or a pharmaceutically acceptable salt thereof, or composition comprising a compound of Formula (I) or a pharmaceutically acceptable salt thereof, to achieve treatment. Anticipated dosages of a compound of Formula (I), or a pharmaceutically acceptable salt thereof, are in the range of 60 to 1000 mg/patient/day. Preferred dosages are anticipated to be in the range of 100 to 800 mg/patient/day. Most preferred dosages are anticipated to be in the range of 130 to 650 mg/patient/day. A therapeutically effective amount can be readily determined by the attending physician, as one skilled in the art, by considering a number of factors known to a person skilled in the art such as, for example, weight, height, age, general health of the patient, severity of the condition, mode of administration, dosing regimen, etc. Although expressed as dosage on a per day basis, the dosing regimen may be adjusted to provide a more optimal therapeutic benefit to a patient. In addition to daily dosing, dosing twice a day (BID) or three times a day may be appropriate. A dosing regimen of BID is presently contemplated as preferred.

The term "treatment" as used herein shall mean slowing the rate or progression of a disease state. It may also include halting the disease state. The term may further include not only halting the disease, but also reducing any disease state that already has occurred. For example, in the context of AAA, the term "treatment" may mean slowing of the expansion rate of an abdominal aortic aneurysm. It may also include stopping the expansion of the abdominal aortic aneurysm. Furthermore, it may include reducing any expansion that has already occurred. In the context of atherosclerosis, the term "treatment" may mean slowing or stopping the progression of atherosclerotic plaque. It may also include reducing existing plaque.

The compound of the present invention is preferably formulated as a pharmaceutical composition and administered by a variety of routes. Preferably, such compositions are for oral administration. Examples and methods for their preparation are well within the knowledge of those skilled in the art. See, for example, Remington: The Science and Practice of Pharmacy (A. Gennaro, et al., eds. 19$^{th}$ ed., Mack Publishing Co., 1995).

The compound of the present invention, and pharmaceutically acceptable salts thereof, may be prepared by a variety of procedures known in the art as well as those described in the Schemes, Preparations, and Examples below. However, the following discussion is not intended to be limiting to the scope of the present invention in any way. For example, the specific synthetic steps for each of the routes described may be combined in different ways, or in conjunction with steps from different Schemes, to prepare the compound, and pharmaceutically acceptable salts, of the present invention. Scheme 2 illustrates an alternate process for synthesizing the compound of the present invention.

The following Preparations and Examples further illustrate the invention and represent typical synthesis of the compound of Formula (I), including any novel intermediate compounds. The reagents and starting materials are readily available to one of ordinary skill in the art or may be made by procedures which are selected from standard techniques of organic and heterocyclic chemistry, techniques which are analogous to the syntheses of known structurally similar compounds, and the procedures described in the Examples below, including any novel procedures.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

The naming of the following Preparations and Examples is generally done using the IUPAC naming feature in Symyx® Draw version 3.2.NET. Alternative names using different naming methodologies may be used to unambiguously identify the Preparations and the compound of Formula (I).

As used herein, the following terms have the meanings indicated: "Bn" refers to benzyl; "DBU" refers to 1,8-diazabicyclo[5.4.0]undec-7-ene; "DMF" refers to dimethylformamide; "DMSO" refers to dimethyl sulfoxide; "EtOAc" refers to ethyl acetate; "EtOH" refers to ethanol; "MeOH" refers to methanol; "NBS" refers to N-bromosuccinimide; and "THF" refers to tetrahydrofuran.

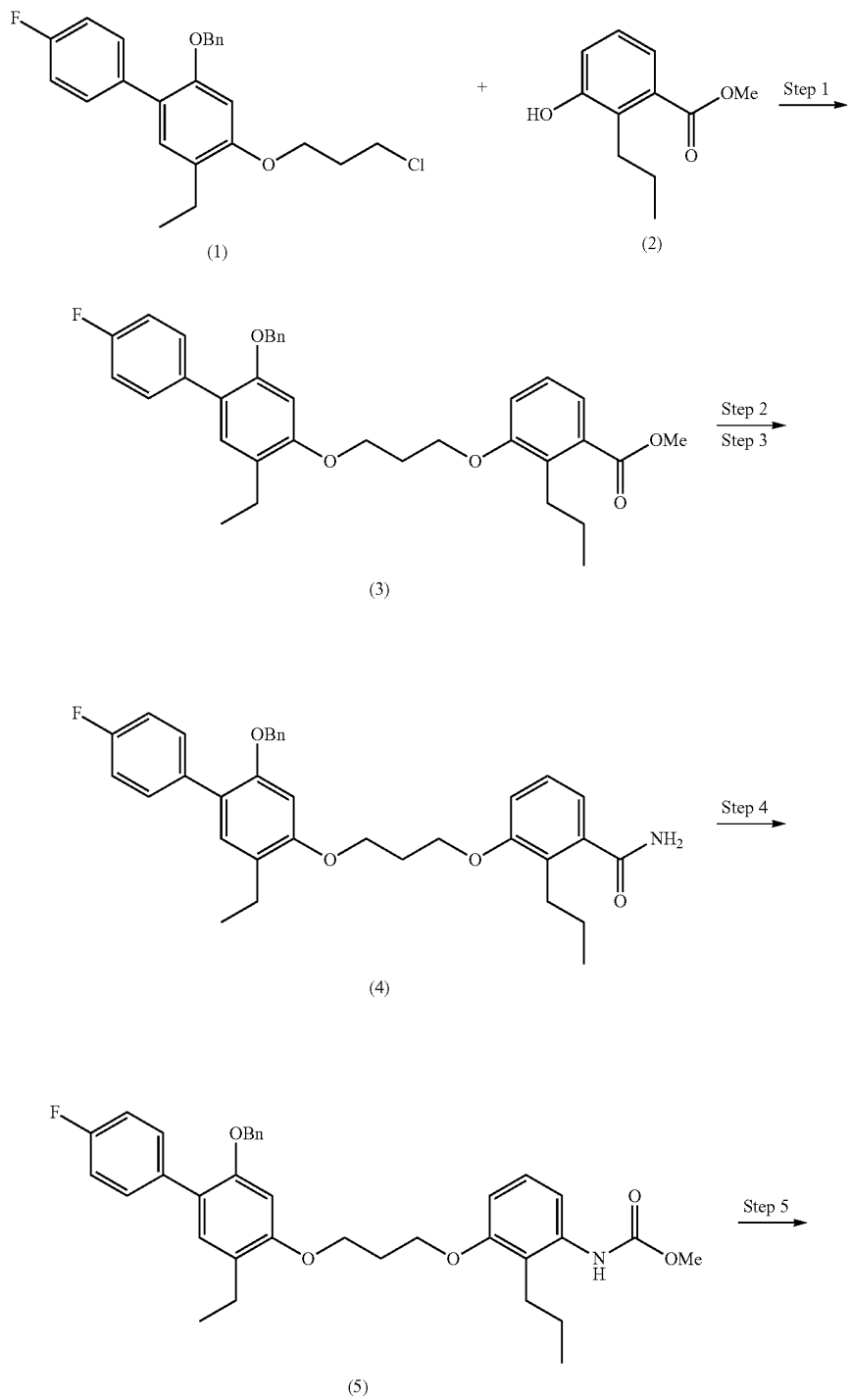

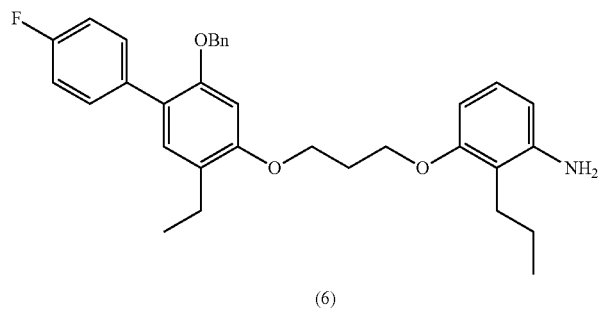

(6)

In Scheme 1 is depicted formation of an intermediate 2-propyl aniline (6).

In Step 1, methyl 3-hydroxy-2-propyl-benzoate (2) is alkylated with 1-benzyloxy-5-(3-chloropropoxy)-4-ethyl-2-(4-fluorophenyl)benzene (1) (prepared according to Org. Process Res. Dev. (2009), 13: 268-275) to provide a methyl propoxy benzoate (3). The skilled artisan will recognize that there are various reaction conditions which will effect such an alkylation. For example, the reaction can be performed in an inert solvent, such as DMSO, in the presence of N,N-dimethylpyridin-4-amine with potassium carbonate as base for 2 to 4 days at about 50 to 90° C. Alternatively the reaction can be performed in DMF, in the presence of potassium iodide, with an inorganic base, such as potassium carbonate or preferably cesium carbonate. The reaction is performed at a temperature of 50 to 110° C. for 8 to 24 h. Other bases that can be used include, for example, sodium hydride.

In Step 2, the methyl benzoate (3) is hydrolyzed to the benzoic acid (not shown) using KOH in N-methylpyrrolidone at a temperature of 90 to 140° C. This is followed, in Step 3, by treatment with thionyl chloride to make the acyl halide and reaction with ammonium hydroxide to obtain the benzamide (4).

In Step 4, the benzamide (4) undergoes a Hofmann rearrangement to give the isocyanate, which in the presence of MeOH as solvent, provides the carbamate (5). The reaction takes place in the presence of a base, such as DBU and a brominating agent, such as NBS. The solvent used is MeOH and the reaction proceeds at a temperature of −10 to 10° C. for a period of 12 to 30 h.

In Step 5, the carbamate (5) is hydrolyzed to the 2-propyl aniline (6) using solid potassium hydroxide in an inert solvent, such as N-methylpyrrolidone at a temperature of 90 to 140° C. for 1 to 8 h.

Methyl 3-hydroxy-2-propyl-benzoate (2) is prepared from 2,3-dimethoxybenzoic acid. The benzoic acid is converted to tert-butyl 2,3-dimethoxybenzoate through the acyl halide. Treatment with a Grignard reagent, propylmagnesium chloride, results in substitution of the ortho methoxy group to provide tert-butyl 3-methoxy-2-propy-benzoate. Deprotection with BBr$_3$ yields 3-hydroxy-2-propyl-benzoic acid which is then esterified to provide methyl 3-hydroxy-2-propyl benzoate (6). An alternate synthesis is available in the literature starting with 3-benzyloxybenzaldehyde (Bioorg. Med. Chem. 1998, 6, 595-604).

Scheme 2

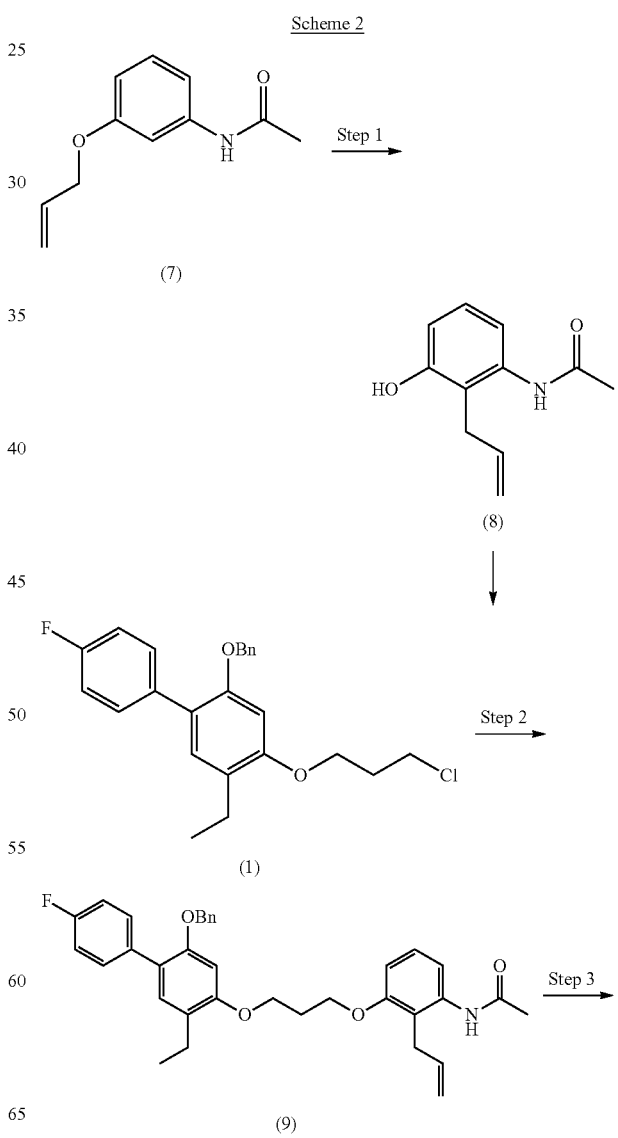

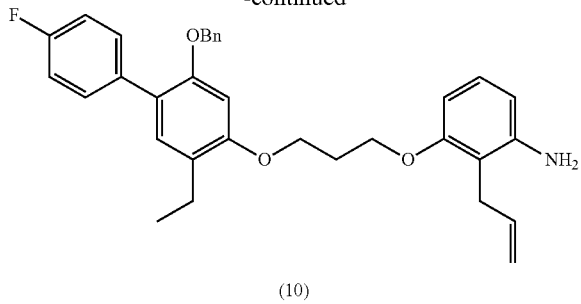

(10)

In Scheme 2 is depicted formation of an intermediate 2-allyl aniline (10).

In Step 1, N-3(-allyloxyphenyl)acetamide (7) undergoes a Claisen rearrangement to provide N-(2-allyl-3-hydroxy-phenyl)acetamide (8). The reaction is performed in a high boiling inert solvent, such as dimethylaniline, at the reflux temperature of the solvent for 12 to 24 h.

In Step 2, N-(2-allyl-3-hydroxy-phenyl)acetamide (8) is alkylated with benzyloxy-5-(3-chloropropoxy)-4-ethyl-2-(4-fluorophenyl)benzene (1) to provide the phenoxy acetamide (9), using conditions previously described for Scheme 1, Step 1.

In Step 3, the phenoxy acetamide (9) is hydrolyzed to give the 2-allyl aniline (10). The reaction proceeds in a solvent mixture of 6 N HCl/ethanol at a temperature of 50° C. to the reflux temperature of the solvent for about 1 to 12 h.

N-3(-allyloxyphenyl)acetamide (7) is prepared by alkylation of acetamidophenol with 3-iodopropene.

Scheme 3

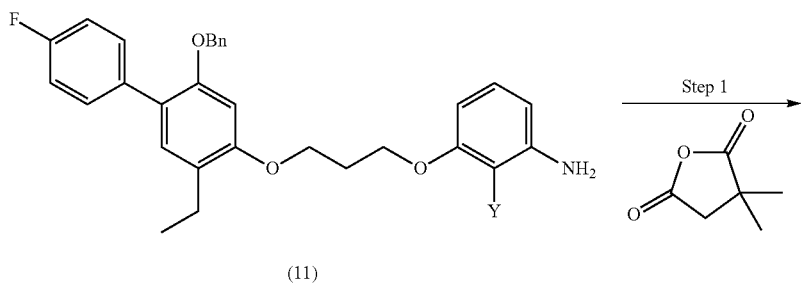

(11)

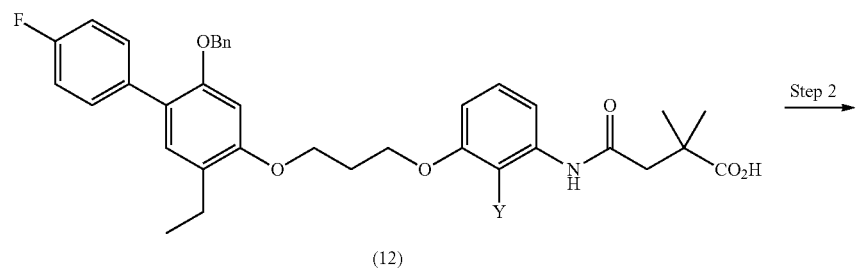

(12)

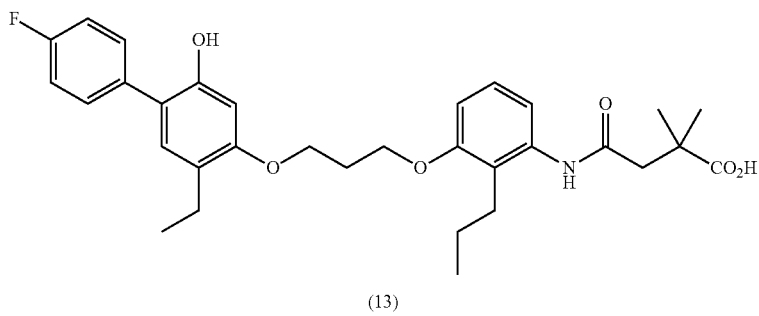

(13)

In Scheme 3 is depicted the synthesis of the compound of the invention (13).

In Step 1, an aniline of formula (11) (Y=allyl or propyl) is acylated with 3,3-dimethyltetrahydrofuran-2,5-dione to provide the amide (12). The reaction is performed in an inert solvent such as dichloromethane or THF. An organic base, such as N-methylmorpholine or diisopropylethylamine, may be added. The reaction proceeds at a temperature of 10 to 40° C. for 6 to 72 h.

In Step 2, the benzyl protecting group of compound (12) is removed using hydrogenation to provide the compound of the invention (13). The reaction proceeds under a hydrogen atmosphere using 5 or 10% palladium on carbon in a solvent or mixture of solvents such as THF, EtOH/THF, EtOH, MeOH, or EtOAc/MeOH. If Y=allyl, then the ally group is reduced to the propyl group under the reaction conditions. If desired, the product can be converted to the sodium carboxylate salt using aqueous NaOH (1 eq) and concentrating under vacuum.

Preparation 1 tert-Butyl 2,3-dimethoxybenzoate

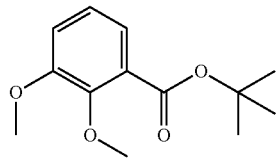 [SMILES: COc1cccc(C(=O)OC(C)(C)C)c1OC]

Add thionyl chloride (67.6 mL, 928 mmol) dropwise to a solution of 2,3-dimethoxybenzoic acid (132 g, 714 mmol) and DMF (1.32 mL) in toluene (528 mL) maintained at 40° C. Stir the solution for 1 h at 40° C. after the addition is complete. Concentrate the mixture in vacuo and dissolve the residue in dichloromethane (528 mL). Warm the mixture to reflux and add tert-butyl alcohol (203.4 mL). Add pyridine (86.6 mL) dropwise over 5 min followed by addition of N,N-dimethylpyridin-4-amine (4.36 g, 35.7 mmol) and stir the mixture 1 h while cooling to ambient temperature. Dilute the mixture with water (200 mL) and acidify the mixture (pH=2) with 2 N hydrochloric acid. Separate the phases and wash the organic phase with 0.5 N hydrochloric acid (2×30 mL). Wash the organic phase with 15% potassium carbonate, water, and brine. Concentrate the organic phase in vacuo to yield the title compound (141.2 g, 83%) as a white solid. ES/MS m/z 165 [M-(C$_4$H$_9$O)]$^+$.

Preparation 2 tert-Butyl 3-methoxy-2-propyl-benzoate

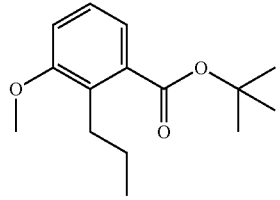 [SMILES: CCCc1c(OC)cccc1C(=O)OC(C)(C)C]

To a chilled solution (−34° C.) of tert-butyl 2,3-dimethoxybenzoate (171 g, 718 mmol) in THF (855 mL) add 2 M propylmagnesium chloride in ether (448.5 mL, 897 mmol) dropwise at a rate sufficient to keep the internal temperature below −10° C. Stir the mixture 3.5 h maintaining the temperature near −12° C. Add acetic acid (51.4 mL) dropwise to the mixture while maintaining the temperature below −10° C. and then dilute with water (340 mL). Separate the phases and extract the aqueous phase with methyl-tert-butylether (3×100 mL). Wash the combined organic extracts with brine and concentrate the organic phase in vacuo to yield the title compound (190 g, quantitative) as a colorless oil containing traces of THF and methyl-tert-butylether. $^1$H NMR (300 MHz, CDCl$_3$) δ 7.24-7.14 (m, 2H), 6.93 (dd, J=1.4, 8.0 Hz, 1H), 3.82 (s, 3H), 2.84-2.79 (m, 2H), 1.59 (m, 11H), 0.97 (t, J=7.4 Hz, 3H).

Preparation 3

3-Hydroxy-2-propyl-benzoic acid

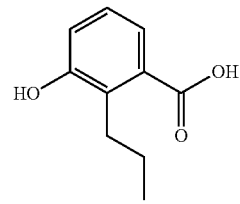

Add boron tribromide (305.6 mL, 305.6 mmol) dropwise while maintaining the temperature below 0° C. to a solution of tert-butyl 3-methoxy-2-propyl-benzoate (61.2 g, 244 mmol) in toluene (428 mL) which has been cooled to −25° C. Stir at −5° C. for 3 h. Add water (100 mL) dropwise, raising the temperature to 7° C., and stir 30 min. Concentrate the mixture in vacuo and then suspend the semisolid in water (200 mL). Stir 1 h and filter the suspension through a glass frit. Wash the collected solid with water and dry the solid to yield the title compound (43.1 g, 98%). $^1$H NMR (300 MHz, CDCl$_3$) δ 7.58 (d, J=8.0 Hz, 1H); 7.16 (t, J=8.0 Hz, 1H); 6.99 (d, J=7.7 Hz, 1H); 5.0 (bs, 2H); 2.98 (t, J=7.7 Hz, 2H), 1.64 (m, 2H); 1.02 (t, J=7.4 Hz, 3H).

Preparation 4

Methyl 3-hydroxy-2-propyl-benzoate

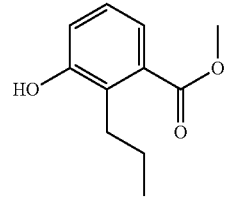

Cool a solution of 3-hydroxy-2-propyl-benzoic acid (59.79 g, 332 mmol) in MeOH (598 mL) to −10° C. and add thionyl chloride (36.26 mL, 497.1 mmol) using a syringe pump over 35 min. Allow the mixture to warm to ambient temperature while stirring over 35 h. Concentrate the mixture in vacuo and dilute the residue with methyl-tert-butylether (360 mL). Concentrate the resultant mixture in vacuo to dryness to yield the title compound (64.4 g, 87%) as a tan solid. ¹H NMR (300 MHz, CDCl₃) δ 7.38 (dd, J=8.0, 0.8 Hz, 1H); 7.10 (t, J=8.0 Hz, 1H); 6.93 (dd, J=8.0, 0.8 Hz, 1H); 5.1 (bs, 1 H); 3.89 (s, 3H); 2.98 (m, 2H); 1.61 (m, 2H); 1.00 (t, J=7.4 Hz, 3H).

Preparation 5

Methyl 3-[3-[5-benzyloxy-2-ethyl-4-(4-fluorophenyl)phenoxy]propoxy]-2-propyl-benzoate

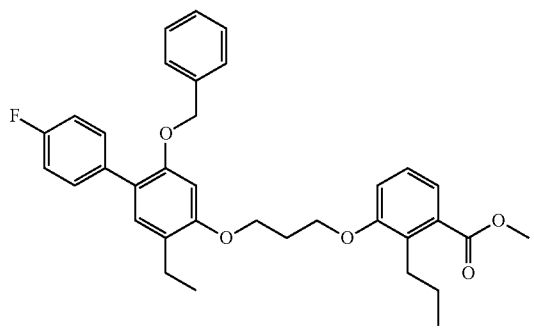 [SMILES: CCCc1c(OCCCOc2cc(OCc3ccccc3)c(-c3ccc(F)cc3)cc2CC)cccc1C(=O)OC]

To a solution of methyl 3-hydroxy-2-propyl-benzoate (40.0 g, 206 mmol) and 1-benzyloxy-5-(3-chloropropoxy)-4-ethyl-2-(4-fluorophenyl)benzene (prepared according to *Org. Process Res. Dev.* (2009), 13: 268-275) (82.15 g, 206 mmol) in dimethylsulfoxide (240 mL) add potassium carbonate (30.2 g, 219 mmol) and N,N-dimethylpyridin-4-amine (2.0 g, 16 mmol) in succession. Stir the suspension for 87 h at 60° C. and then allow it to cool. Dilute the mixture with water (600 mL) and with methyl-tert-butylether (100 mL) and stir for 15 min. Separate the phases and wash the aqueous portion with methyl-tert-butylether (3×30 mL). Wash the combined organic extracts with water and brine. Concentrate the organic portion in vacuo to yield the title compound (123.0 g, quantitative) as a brown oil. ES/MS m/z 557 (M+1).

Preparation 6

3-[3-[5-Benzyloxy-2-ethyl-4-(4-fluorophenyl)phenoxy]propoxy]-2-propyl-benzoic acid

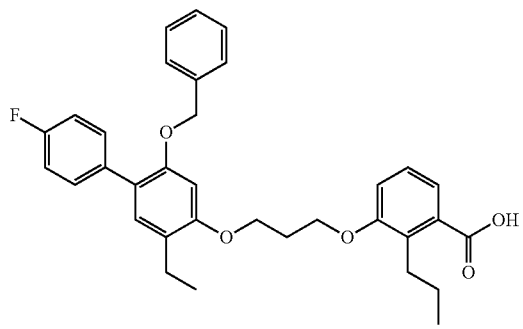 [SMILES: CCCc1c(OCCCOc2cc(OCc3ccccc3)c(-c3ccc(F)cc3)cc2CC)cccc1C(=O)O]

To a solution of methyl 3-[3-[5-benzyloxy-2-ethyl-4-(4-fluorophenyl)phenoxy]propoxy]-2-propyl-benzoate (119 g, 181 mmol) in N-methylpyrrolidone (476 mL), add potassium hydroxide (21.2 g, 378 mmol) and stir 25 min at 120° C. Allow the mixture to cool and then dilute with water (240 mL) and methyl-tert-butylether (100 mL). Adjust to pH=2.5 with 12 N hydrochloric acid. Separate the phases and wash the aqueous phase with methyl-tert-butylether (3×35 mL). Wash the combined organic extracts twice with water and once with brine. Concentrate the organic extracts in vacuo. Recrystallize the resultant residue from acetonitrile, filter, and dry to yield (78 g, 67%) as a white solid. ¹H NMR (300 MHz, CDCl₃) δ 7.60-7.47 (m, 3H); 7.37-7.20 (m, 6H); 7.12-7.02 (m, 4H); 6.60 (s, 1 H); 5.00 (s, 2H); 4.20 (m, 4H); 3.00 (m, 2H); 2.61 (q, J=7.7 Hz, 2H); 2.33 (m, 2H); 1.59 (m, 2H); 1.18 (t, J=7.7 Hz, 3H); 0.98 (t, J=7.7 Hz, 3H).

Preparation 7

3-[3-[5-Benzyloxy-2-ethyl-4-(4-fluorophenyl)phenoxy]propoxy]-2-propyl-benzamide

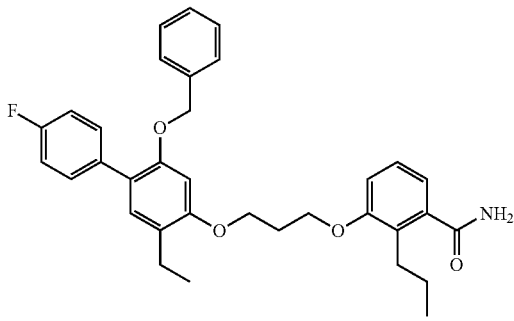 [SMILES: CCCc1c(OCCCOc2cc(OCc3ccccc3)c(-c3ccc(F)cc3)cc2CC)cccc1C(N)=O]

Add thionyl chloride (8.22 mL, 113 mmol) dropwise to a solution of 3-[3-[5-benzyloxy-2-ethyl-4-(4-fluorophenyl)phenoxy]propoxy]-2-propyl-benzoic acid (50.0 g, 92 mmol) and DMF (2.5 mL, 32 mmol) in THF (250 mL). Stir for 1 h and then add the reaction to a solution of ammonium hydroxide (102.5 mL, 1.52 mol) at 0-5° C. Add MeOH (250 mL) and water (500 mL) in a dropwise fashion. Concentrate to about one half the volume in vacuo and stir the resulting suspension 30 min at 0-5° C. Filter the suspension on a glass frit and dry the resulting solids under vacuum to provide the title compound (50.3 g, quantitative) as an off-white solid. ES/MS m/z 542 (M+1).

Preparation 8

Methyl N-[3-[3-[5-benzyloxy-2-ethyl-4-(4-fluorophenyl)phenoxy]propoxy]-2-propyl-phenyl]carbamate

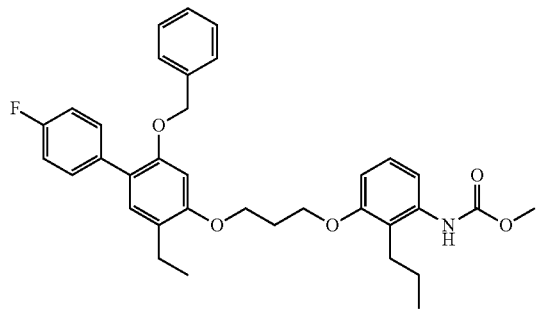 [SMILES: CCCc1c(NC(=O)OC)cccc1OCCCOc1cc(OCc2ccccc2)c(-c2ccc(F)cc2)cc1CC]

Sequentially add 1,8-diazabicyclo[5.4.0]undec-7-ene (51.6 mL, 345 mmol) and N-bromosuccinimide (34.6 g, 194 mmol) to a mechanically stirred suspension of 3-[3-[5-benzyloxy-2-ethyl-4-(4-fluorophenyl)phenoxy]propoxy]-2-propyl-benzamide (62.0 g, 114 mmol) in MeOH (620 mL) during which time the temperature raises from −4.1° C. to −3.2° C. over 1 min. Stir the reaction at −5° C. to −10° C. for 22 h. Add a solution of sodium bisulfate (25.1 g, 209 mmol, in 25 mL water) dropwise with stirring. Add water (620 mL) dropwise and stir 30 min at 10° C. Filter the suspension on a glass frit, wash the collected solid with water, and dry under vacuum to yield the title compound (65.8 g, quantitative) as an off-white powder. ES/MS m/z 572 (M+1).

Preparation 9

3-[3-[5-Benzyloxy-2-ethyl-4-(4-fluorophenyl)phenoxy]propoxy]-2-propyl-aniline hydrochloride Add potassium hydroxide (12.97 g, 231 mmol) to a solution of methyl N-[3-[3-[5-benzyloxy-2-ethyl-4-(4-fluorophenyl)phenoxy]propoxy]-2-propyl-phenyl]carbamate (65.8 g, 115 mmol) in N-methylpyrrolidone (203 mL) and stir at 110-120° C. for 2 h. Allow the mixture to cool and then pour it into a mixture of water (450 mL) and methyl-tert-butylether (180 mL). Stir the mixture 20 min and separate the phases. Extract the aqueous phase with additional methyl-tert-butylether (3×50 mL). Filter the combined organic extracts through a glass frit and wash the filtrate with 15% brine solution. Concentrate the filtrate in vacuo and dissolve the residue in a mixture of ethyl acetate (300 mL) and methyl-tert-butylether (300 mL). Add 4 N hydrochloric acid (43.1 mL) dropwise to this solution while stirring and cooling the resultant suspension with an ice/salt bath. Collect the solid by filtration on a glass frit, wash with cold methyl-tert-butylether, and dry under vacuum to yield the title compound (57.8 g, 91%) as an off-white solid. ES/MS m/z 514 (M+1, free base).

Preparation 10

4-[[3-[3-[5-Benzyloxy-2-ethyl-4-(4-fluorophenyl)phenoxy]propoxy]-2-propyl-phenyl]amino]-2,2-dimethyl-4-oxo-butanoic acid

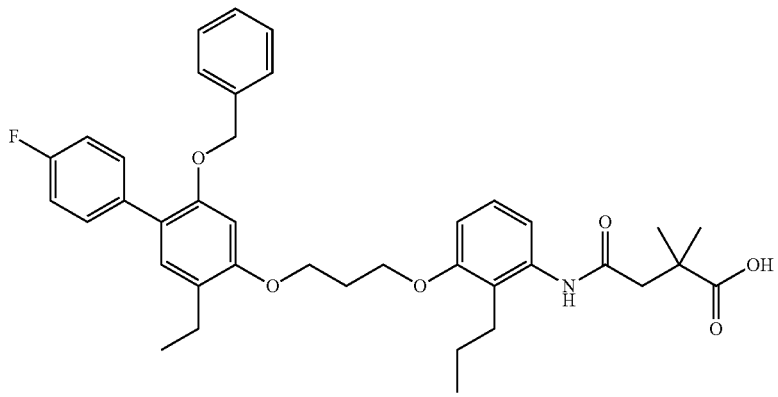 [SMILES: CCCc1c(NC(=O)CC(C)(C)C(=O)O)cccc1OCCCOc1cc(OCc2ccccc2)c(-c2ccc(F)cc2)cc1CC]

Add diisopropylethylamine (57 mL, 327 mmol) to a suspension of 3-[3-[5-benzyloxy-2-ethyl-4-(4-fluorophenyl)phenoxy]propoxy]-2-propyl-aniline hydrochloride (90 g, 175 mmol) in THF (450 mL). To this mixture, add dihydro-3,3-dimethyl-2,5-furandione (32.1 g, 251 mmol) and stir at 35° C. until LCMS indicates 5% starting material remaining. Concentrate the mixture in vacuo and add methyl tert-butyl ether (100 mL) and water (75 mL). Adjust to pH=2-3 with phosphoric acid and separate the layers. Wash the aqueous layer with additional methyl tert-butyl ether (2×50 mL). Wash the combined organic extracts with brine and concentrate in vacuo. Dissolve the crude residue in methyl tert-butyl ether (180 mL) and add hexane (450 mL) to obtain a suspension and stir for 30 min. Collect the suspension by filtration and dry to yield the title compound (92.5 g, 88%) as a white solid. ES/MS m/z 642 (M+1).

EXAMPLE 1

4-[[3-[3-[2-ethyl-4-(4-fluorophenyl)-5-hydroxy-phenoxy]propoxy]-2-propyl-phenyl]amino]-2,2-dimethyl-4-oxo-butanoic acid

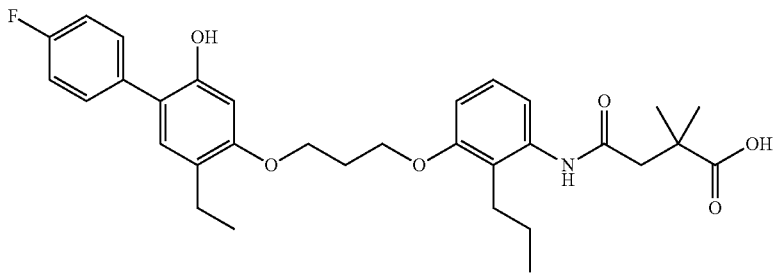 [SMILES: CCCc1c(NC(=O)CC(C)(C)C(=O)O)cccc1OCCCOc1cc(O)c(-c2ccc(F)cc2)cc1CC]

Hydrogenate a slurry of 10% palladium on charcoal, 50% wet (with water by weight) (13 g) and 4-[[3-[3-[5-benzyloxy-2-ethyl-4-(4-fluorophenyl)phenoxy]propoxy]-2-propyl-phenyl]amino]-2,2-dimethyl-4-oxo-butanoic acid (260 g, 405 mmol)) in THF (1560 mL) starting at a hydrogen pressure of 900 psi. Continue the hydrogenation 20 h while not adding additional hydrogen. Hydrogenate two additional days maintaining hydrogen pressure of 200 psi. Filter the mixture through diatomaceous earth and concentrate the filtrate in vacuo to yield the title compound (251 g, quantitative) as a solid. Excess weight is due to the presence of THF. ES/MS m/z 552 (M+1).

EXAMPLE 2

Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate Add 1 N sodium hydroxide (404 mL) dropwise to a solution of 4-[[3-[3-[2-ethyl-4-(4-fluorophenyl)-5-hydroxy-phenoxy]propoxy]-2-propyl-phenyl]amino]-2,2-dimethyl-4-oxo-butanoic acid (223 g, 404 mmol) in THF (1115 mL) and stir at ambient temperature for 15 min. Reduce the volume in vacuo and add water (1300 mL). Remove additional solvent using a membrane pump, to avoid heating the solution, to obtain a final volume of 1250 mL. Lyophilize the remaining solution in batches to yield the title compound (230 g, 99%) as an off-white solid. ES/MS m/z 552 (M+1, free base).

Animal studies have increasingly implicated the leukotriene synthesis pathway in chronic inflammatory diseases, including atherosclerosis and AAA. Poeckel, et al. *Cardiovascular Research* (2010), 86: 243-253. Atherosclerosis is a condition in which an atherosclerotic plaque or lesion forms and builds in the intima of arteries. It is a chronic inflammatory response of the walls of arteries primarily caused by the accumulation of macrophage white blood cells and promoted by low-density lipoproteins without adequate removal of fats and cholesterol from the macrophages by functional high density lipoproteins. The artery becomes inflamed. $LTB_4$ plays a proatherogenic role in atherosclerosis because of its ability to promote the adhesion and chemotaxis of leukocytes across the endothelium. Bäck, *Current Atherosclerosis Reports* (2008), 10: 244-251; Aiello et al. *Arterioscler. Thromb. Vasc. Biol.* (2002) 22: 443-449; Rosenfeld, *Arterioscler. Thromb. Vasc. Biol.* (2002) 22: 361-363. The cholesterol plaque causes the muscle cells to enlarge and form a hard cover over the affected area. Spanbroek et al. *PNAS*, (2003), 100(3): 1238-1243.

Stable atherosclerotic plaques, which tend to be asymptomatic, are rich in extracellular matrix and smooth muscle cells. Unstable plaques are rich in macrophages and foam cells and the extracellular matrix separating the lesion from the arterial lumen (fibrous cap) is typically weak and prone to rupture. Ruptures of the fibrous cap expose thrombogenic material, such as collagen, to the circulation and eventually induce thrombus formation in the lumen. Upon formation, intraluminal thrombi may occlude arteries outright or may detach, move into the circulation and eventually occlude smaller downstream arterial branches causing thromboembolism (Ross, *N. Engl. J. Med.* (1999), 340(2): 115-126).

A degenerative disorder, AAA is characterized by relentless progression of 1) inflammation of the aortic wall; 2) uncontrolled local production of destructive proteases; 3) destruction of structural proteins; and 4) depletion of medial smooth muscle cells. The early or acute phase begins with recruitment of inflammatory cells in the media and adventitia. Intramural injury results when local reactive oxygen, leukotrienes, chemokines and matrix degradation products act in concert to activate various protease systems. These pathological changes in the aortic wall lead to segmental weakening, progressive dilation, and spontaneous rupture (Nanda et al. *Recent Patents on Cardiovascular Drug Discovery* (2009), 4: 150-159).

Chronic transmural inflammation is one of the principal histologic features of established AAA's. This inflammatory response consists of mononuclear phagocytes, lymphocytes, and blood plasma cells. The nature of the chronic inflammation response in AAA appears to differ from that observed in atherosclerosis. The inflammatory response in AAA's is usually transmural in distribution, with dense infiltrates largely focused in the outer media and adventitia. In atherosclerosis, infiltrating inflammatory cells are primarily confined to the diseased intima, and they do not appear to become as concentrated or extensively distributed as in AAAs. Despite the common chronic inflammation component, the destruction of structural proteins in the outer aortic wall, not seen in atherosclerosis, appears to be responsible for aneurysmal degeneration (Thompson et al. *Curr. Probl. Surg.* (2002), 39(2): 110-230, at 115, 137 and 142).

Although there are published studies to the contrary (See, for example, Cao et al. *Prostaglandins & other Lipid Mediators*, (2007) 84: 34-42), a majority of published studies are believed to support the role of the 5-lipoxygenase pathway, and $LTB_4$, in AAA pathogenesis. Elevated levels of $LTB_4$ derived from neutrophils play a key role in the pathogenesis of AAA (Houard et al. *FASEB J.* (2009), 23: 1376-1383; Ahluwalia, et al. *J. Immunol.* (2007), 179: 691-697; Kristo et al. *Atherosclerosis*, (2010), 210: 107-113).

The following in vitro and in vivo studies demonstrate the activity and efficacy of the compound of Formula (I), or the sodium salt thereof, in treating atherosclerosis and AAA by antagonizing $LTB_4$. These assays are generally recognized by those skilled in the art as indicative of human clinical therapeutic activity. Assays evidencing $LTB_4$ signaling antagonism activity and efficacy may be carried out substantially as follows or by similar assays affording similar data.

In Vitro Assay Procedures:

BLT1 binding and activation by $LTB_4$ increases intracellular inositol 1,4,5-triphosphase levels that leads to intracellular calcium release and calcium influx is mediated by coupling with and signaling through specific G-protein coupled signal transduction pathway subunits (Gaudreau et al. *Biochem. J.* (1998), 335 (Pt 1): 15-18). Following are two in vitro assays used to demonstrate Example 2 antagonism of the BLT1 proximal signaling cascade events: a [$^3$H]-$LTB_4$ ligand displacement assay using membrane preparations generated from BLT1 and BLT2 stable cell lines and a whole cell calcium mobilization assay.

$LTB_4$ Ligand Displacement Assay

[$^3$H]-$LTB_4$ and known BLT1 and BLT2 antagonists are used to generate $LTB_4$ displacement curves and $IC_{50}$ values for compounds of the present invention. Receptor inhibition by compounds of the present invention is determined relative to BLT1 inhibitor and BLT2 inhibitor reference molecules to obtain percent efficacies.

hBLT1 Test Compound Preparations: For hBLT1 assays, test compounds are prepared in DMSO to make up a 10 mM stock solution. The stock solution is initially diluted 1:10 in Buffer A (50 mM 4-(2-hydroxyethyl)piperazine-1-ethanesulfonic acid (HEPES) pH 7.4, 10 mM $MgCl_2$, 10 mM NaCl, 10% glycerol (v/v), 1% bovine serum albumin (BSA) (w/v)), followed by 3× serial dilutions in Buffer B (50 mM HEPES pH 7.4, 10 mM $MgCl_2$, 10 mM NaCl, 10% glycerol (v/v), 1% BSA (w/v), 10% DMSO (v/v)) creating a ten-point dilution curve. Final compound concentrations ranging from 30 μM to 1.52 nM are plated in a 96-well round-bottom plate for conducting the in vitro assays.

hBLT2 Test Compound Preparations: For hBLT2 assays, test compounds are prepared in DMSO to make up a 10 mM stock solution. The stock solution is initially diluted 1:10 in Buffer A (50 mM HEPES pH 7.4, 10 mM $MgCl_2$, 10 mM NaCl, 10% glycerol (v/v), 1% BSA (w/v)), followed by 3× serial dilutions in Buffer B (50 mM HEPES pH 7.4, 10 mM $MgCl_2$, 10 mM NaCl, 10% glycerol (v/v), 1% BSA (w/v), 10% DMSO (v/v)) creating a ten-point dilution curve. Final compound concentrations ranging from 300 μM to 15.2 nM are plated in a 96-well round-bottom plate for conducting the in vitro assays.

Methods for Generation of BLT1/CHO-K1 and BLT2/CHO-K1 Stable Cell Lines:

Generally, these cell lines are generated using commercially available materials and by procedures known to those skilled in the art.

hBLT1/CHO-K1 Stable Xcell Line Preparations: Human BLT1 receptor DNA (National Center for Biotechnology Information (NCBI), Reference Sequence NM_181657) is synthesized and cloned into expression vector pcDNA3.1/Hygro(+) (Invitrogen V87020). The cDNA expression vector construct is transfected into Chinese hamster ovary (CHO-K1) cells (American Type Culture Collection (ATCC) CCL-61) using Lipofectamine 2000 (Invitrogen) as transfection reagent. Cells are cultured in selective Dulbecco's Modified Eagle Medium (DMEM) containing 200 μg/mL Hygromycin, 24 hours post transfection. Single clones are isolated and screened for BLT1 expression and function using Western Blot analysis and Fluorometric Imaging Plate Reader (FLIPR®) calcium release assay.

hBLT2/CHO-K1 Stable Cell Line Preparations: Human BLT2 short form receptor DNA (National Center for Biotechnology Information (NCBI), Reference Sequence GenBank AB029892, which is 32 amino acids shorter than the long form BLT2 on the N-terminus, Wang et al. *J. Biol. Chem.* (2000), 275 (52): 40686-40694) is synthesized and cloned into expression vector pcDNA3.1/Hygro(+) (Invitrogen V87020). The cDNA expression vector construct is transfected into CHO-K1 cells (ATCC CCL-61) using Lipofectamine 2000 (Invitrogen) as transfection reagent. Cells are cultured in selective DMEM medium containing 200 μg/mL Hygromycin, 48 h post transfection. Single clones are isolated and screened for BLT2 expression and function using Western Blot analysis and FLIPR® calcium release assay.

hBLT1 Membrane Preparations: hBLT1 transfected CHO-K1 cells are suspended in 50 mM HEPES pH 7.4, 10 mM $MgCl_2$, 10 mM NaCl buffer, sonicated, and concentrated by differential centrifugation. Briefly, after sonification, the homogenates are centrifuged at 1000×g for 10 min. Supernatants are recovered and centrifuged again at 50,000×g for 60 min. The pellet is collected, resuspended in buffer containing 50 mM HEPES at pH 7.4, 10 mM $MgCl_2$, 10 mM NaCl, 10% glycerol and used as the hBLT1 membrane.

hBLT2 Membrane Preparations: hBLT2 transfected CHO-K1 cells are suspended in 50 mM HEPES pH 7.4, 10 mM $MgCl_2$, 10 mM NaCl buffer, sonicated, and concentrated by differential centrifugation. Briefly, after sonification, the homogenates are centrifuged at 1000×g for 10 min. Supernatants are recovered and centrifuged again at 50,000×g for 60 min. The pellet is collected, resuspended in buffer containing 50 mM HEPES pH 7.4, 10 mM MgCl$_2$, 10 mM NaCl, 10% glycerol and used as the hBLT2 membrane.

[$^3$H]-LTB$_4$ Binding Assay in hBLT1 Containing Membranes:

[$^3$H]-LTB$_4$ (30 μL of 1.3 nM, PerkinElmer NET-852) is aliquoted into a 96-well Millipore Multiscreen-filter binding plate (catalogue number MAFBNOB10) which is pre-wetted with Buffer A (50 mM HEPES pH 7.4, 10 mM MgCl$_2$, 10 mM NaCl, 10% glycerol, 1% BSA). A previously prepared dose response range of test compound (10 μL) is then added in columns 2-11, with final compound concentrations ranging from 3 μM to 152 pM. For binding controls, aliquots of sodium 2-[3-[3-[(5-ethyl-4'-fluoro-2-hydroxy[1,1'-biphenyl] 4-yl)oxy]propoxy]-2-propylphenoxy]-benzoate (LY293111 Na, a commercially available known hBLT1 inhibitor; Sawyer et al. *J. Med. Chem.* (1995), 38: 4411-4432, compound 43b) (10 μL of 3 μM, final concentration) are added (as a positive control) or 10 μL of Buffer B (50 mM HEPES pH 7.4, 10 mM MgCl$_2$, 10 mM NaCl, 10% glycerol, 1% BSA, 10% DMSO) (negative control) into selected wells. hBLT1 membrane protein (0.7 μg) is added to appropriate wells of the microtiter plate for a total volume of 100 μL. The plate is placed on a plate mixer at low speed and incubated for 1 h. After incubation, the plate is aspirated and then washed with 200 μL of ice cold Buffer C (50 mM HEPES pH 7.4, 10 mM MgCl$_2$, 10 mM NaCl) followed by an additional 2×100 μL washes, aspirating between washes. The plate is air dried, and then Microscint® 20 (PerkinElmer) (100 μL) is added. The plate is allowed to sit for 16 h and then read on a Packard Instrument Company Topcount® for 1 min. CPMs (Counts per minute) are plotted versus inhibitor concentration and a curve fitted with a 3-parameter logistic fit with fixed bottom to obtain IC$_{50}$ values. The IC$_{50}$s are converted to K$_i$ values by dividing by 2.7 (previously calculated). (2.7 is a constant previously determined by running a saturation binding curve with [$^3$H]-LTB$_4$ and hBLT1 and determining the K$_M$, using the formula Ki=IC$_{50}$/1+[Substrate]/K$_M$ and simplifying Ki=IC$_{50}$/2.7).

Following a protocol essentially as described above, the compound of Example 2 displayed an absolute Ki of 5.5 nM (relative Ki of 10.4 nM) under these conditions. These data evidence potent antagonism of LTB$_4$ by the compound of Example 2 at the high affinity LTB$_4$ receptor.

[$^3$H]-LTB$_4$ Binding Assay in hBLT2 Containing Membranes:

[$^3$H]-LTB$_4$ (30 μL of 2.8 nM, PerkinElmer NET-852) is aliquoted into each well of a Falcon® 3072 microtiter plate (BD Biosciences). A previously prepared 10 point dose response range of test compound (10 μL) is then added in columns 2-11, with final compound concentrations ranging from 30 μM to 1.5 nM. For binding controls, aliquots of 1-(5-ethyl-2-hydroxy-4-(6-methyl-6-1H-tetrazol-5-yl)heptyloxy)phenyl)ethanone (LY255283, a commercially available known hBLT2 inhibitor) (10 μL of 100 μM, final concentration of 10 μM) are added (as a positive control) or 10 μL of Buffer B (50 mM HEPES pH 7.4, 10 mM MgCl$_2$, 10 mM NaCl, 10% glycerol, 1% BSA, 10% DMSO) (negative control) into selected wells. hBLT2 membrane protein (7.5 μg) is added to the appropriate wells of the microtiter plate for a total volume of 100 μL. The plates are placed on a plate mixer at low speed and incubated for 1 h. After incubation, 90 μL from each well of the reaction mixture is transferred to a 96-well Millipore Multiscreen-filter binding plate (catalogue number MAFBNOB10), which is pre-wet with Buffer A (50 mM HEPES pH 7.4, 10 mM MgCl$_2$, 10 mM NaCl, 10% glycerol, 0.03% BSA). The plate is aspirated and then washed 3 times with 300 μL ice cold Buffer C (50 mM HEPES pH 7.4, 10 mM MgCl$_2$, 10 mM NaCl), aspirating after each wash step. The plate is air dried, and then Microscint® 20 (PerkinElmer)(100 μL) is added. The plate is allowed to sit for 16 h and then read on a Packard Instrument Company Topcount® for 1 min. CPMs (Counts per minute) are plotted versus inhibitor concentration and a curve fitted with a 3-parameter logistic fit with fixed bottom to obtain IC$_{50}$ values.

Following a protocol essentially as described above, the compound of Example 2 displayed an absolute IC$_{50}$ of 16.5 μM (relative IC$_{50}$ of 15.4 μM) under these conditions. These data evidence statistically insignificant antagonism of LTB$_4$ by the compound of Example 2 at the low affinity LTB$_4$ receptor.

FLIPR® Calcium Release Assay

Chinese hamster ovary (CHO-K1) cells stably expressing the high-affinity (BLT1) LTB$_4$ receptor are seeded at 10,000 cells/well in a 96 well plate (Corning) in growth medium containing DMEM/F-12 (3:1) w/o phenol red (Invitrogen), 5% fetal bovine serum (FBS) (Hyclone), 20 mM HEPES (Invitrogen), 200 μg/mL Hygromycin B (Invitrogen) and 40 μg/mL L-Proline (Sigma). The plate is incubated for 22-24 h at 37° C. 5% CO$_2$ then growth medium is replaced with 50 μL/well of test medium containing Roswell Park Memorial Institute (RPMI) RPMI-1640 w/o phenol red, 20 mM HEPES (both from Invitrogen), and 0.2% w/v Bovine Serum Albumin (Sigma). After 30-60 min of incubation at 37° C. 5% CO$_2$, 50 μL of diluted FLIPR Calcium 3 Assay Kit reagent (Molecular Devices) containing 5 mM probenecid (Sigma) are added to wells and the plate is incubated for an additional 1.25 h at 37° C. 5% CO$_2$. The plate is placed in FLIPR® instrument (Molecular Devices) and 50 μL of 4% v/v DMSO or compound is added followed 6 min later by 50 μL of vehicle or LTB$_4$. Final concentration of LTB$_4$ is 8 nM. The plate is read using a 0.5 second exposure length and 0.6 Watt laser power.

The compound of Example 2 evidenced an inhibition of LTB$_4$-induced calcium mobilization (potency and selectivity) Kb (nM) of 0.98 (n of 2; +/−1.64) and a relative IC$_{50}$ (nM) of 6.48 (n of 2; +/−10.8).

Further, below are several additional assays used to measure downstream events that are induced by LTB$_4$ binding to BLT1, including phosphorylation of extracellular signal-regulated kinases 1 and 2 (ERK) in monocytes (Lindsay et al. *J. Leukoc. Biol.* (1998), 64: 555-562), and induction of CD11b in neutrophils in relevant cell types in mouse and human blood as well as LTB$_4$ binding affinity to the nuclear receptor subfamily of peroxisome proliferator activated receptors (PPAR).

Human Phosphorylated Extracellular-Related Kinase (pERK) Assay

The ability of the compound of Example 2 to block LTB$_4$-induced signaling through BLT1 was assessed in whole blood obtained from healthy human volunteers and from 129SvEv mice that are the model strain for preclinical AAA efficacy evaluation.

Whole blood is collected from human donors in 10 mL K2 ethylenediaminetetraacetic acid (EDTA) vacutainer tubes (BD Biosciences). Aliquots of whole blood are pre-warmed at 37° C. for 20 min. 10 point dose response curves of test compounds are assayed at final concentrations of 20 nM-10 μM. 10 point ½ serial dilutions of compound at 1000× of final assayed concentration are prepared in DMSO. Compound is then diluted to 10× in Dulbecco's Phosphate Buffered Saline (DPBS) (DMSO concentration is now 1%). 10 μL of compound dilutions (at 10× in DPBS) or 1% DMSO in DPBS are added to wells of a 2.0 mL volume 96 deep well plate (Nunc) and placed in 37° C. heat block.

Immediately thereafter, 80 μL whole blood is added and incubated for 20 min at 37° C. (10 μL anti-human CD14-FITC from BD Biosciences is added for final 10 min) 11 μL of pre-warmed 10×$LTB_4$ from Cayman Chemicals (final concentration 10 nM) is added and incubated at 37° C. for 1 min. The reaction is stopped with 1.5 mL of 1× Phosflow Lyse/Fix from BD Biosciences (pre-warmed to 37° C.). The plate is sealed, vortexed, and incubated at 37° C. for 10 min. Cells are washed once with 1.5 mL DPBS (Hyclone) then permeablized with 100 μL of 2% Cytofix (BD Biosciences) +900 μL cold methanol for 30 min on ice. The cells are washed once with 1 mL wash buffer (Dulbecco's Phosphae-Buffered Saline (DPBS)+5% FBS) then incubated with 100 μL pERK antibody (Cell Signaling diluted 1:100) for 1 h at room temperature. Cells are washed once with wash buffer then incubated with 100 μL of 2 μg/mL anti-rabbit IgG-PE (Invitrogen) for 30 min at room temperature in the dark. The cells are washed again with wash buffer then fixed in 400 μL 1% Cytofix (BD Biosciences). Cells are transferred to 12×75 tubes and then refrigerated until analysis. Samples are warmed to room temperature and analyzed on a Beckman Coulter FC500 flow cytometer. Human monocytes are isolated by gating strategy side scatter vs CD14-FITC positive. Data are analyzed with WinList software (Verity Software House) to determine mean and median fluorescent intensity values for pERK-PE from monocyte population.

When the compound of Example 2 is added to human whole blood at varying concentrations, $LTB_4$-induced phosphorylation of ERK in monocytes is blocked with an $IC_{50}$ of 814 nM evidencing antagonism of downstream signaling events by the compound of Example 2.

Mouse pERK Assay

Whole blood is collected from 129SvEv mice in 50 mM EDTA (Gibco). For in vitro experiments, 10 point dose response curves of test compounds are assayed at final concentrations of 20 nM-10 μM. 10 point ½ serial dilutions of compound at 1000× of final assayed concentration are prepared in DMSO. Compound is then diluted to 10× in DPBS (DMSO concentration is now 1%). 10 μL of compound dilutions (at 10× diluted in DPBS) or 1% DMSO in DPBS are added to wells of a 96 deep well plate. 80 μL whole blood is added and incubated for 20 min at room temperature (10 μL of anti-mouse LY6G-FITC antibody (BD Pharmingen) and 10 μl of anti-mouse CD11b-APC BD Biosciences at 1 μg/mL final concentrations are added for final 10 min) 11 μL of 10× pre-warmed $LTB_4$ (final concentration 20 nM) is added and incubated at 37° C. for 2 min. Reaction is stopped with 1.5 mL of 1× Phosflow Lyse/Fix from BD Biosciences (pre-warmed to 37° C.). The plate is sealed, vortexed, and incubated at 37° C. for 10 min. Cells are washed once with 1.5 mL DPBS then permeablized with 1 mL BD Perm/Wash buffer (BD Biosciences) for 10 min at room temperature. Cells are washed once with 1 mL Perm/Wash buffer, then incubated with 100 μl pERK antibody (Cell Signaling diluted 1:100) for 1 h at room temperature. Cells are washed again with Perm/Wash buffer then incubated with 100 μL of 2 μg/mL anti-rabbit IgG-PE (Invitrogen) for 30 min at room temperature in the dark. Cells are washed again with Perm/Wash buffer and then fixed in 400 μL 1% BD Cytofix. Mouse monocytes are isolated by gating strategy LY6G-FITC negative/CD11b-APC positive.

The compound of Example 2 blocked $LTB_4$-induced phosphorylation of ERK in mouse whole blood monocytes with an $IC_{50}$ of 243 nM evidencing antagonism of downstream signaling events.

CD11b Assay

Inflammation is one pathophysiological process amenable to the development of biomarkers. For example, a simple blood test may serve as a surrogate to a tissue biopsy to monitor neutrophil activation. Neutrophil activation leads to their migration from the blood to the site of tissue damage and is central to the inflammatory process (Busse, *Am. J. Respir. Crit Care Med.* (1998), 157: S210-213), and neutrophils are typically absent in healthy tissues. An assay based on a biomarker that is specific to neutrophil activation in blood is a less-invasive indicator of an inflammatory response in tissue. Increased expression of the β2 integrin CD11b/CD18 (Mac-1), a glycoprotein on the neutrophil surface, is an early step in the migration of neutrophils into the area of inflammation (Parkos, *BioEssays* (1997), 19: 865-873). The utility of CD11b as a preclinical and clinical biomarker of BLT1 receptor antagonism is based on the fact that $LTB_4$ potently upregulates CD11b expression on neutrophils (Turner et al. *J. Clin. Invest.* (1996), 97: 381-387), and stimulation of CD11b by $LTB_4$ has been shown to be reduced significantly by antagonists of the $LTB_4$ receptor (Allen et al. *J. Pharmacol. Exp. Ther.* (1996), 277: 341-349; Davis et al. *J. Immunol. Methods* (2000), 240: 125-132; Marder et al. *Biochem. Pharmacol.* (1995), 49: 1683-1690).

EDTA anti-coagulated blood is collected from human donors or mice as before. For in vitro experiments, 8 or 10 point dose response curves of test compounds are assayed at final concentrations of 78 nM-10 μM or 20 nM-10 μM respectively. ½ serial dilutions of compound at 1000× of final assayed concentration are prepared in DMSO. Compound is then diluted to 10× in DPBS (DMSO concentration is now 1%). 10 μL of compound dilutions (at 10× in DPBS) or 1% DMSO in DPBS are added to wells of a 96 deep well plate. 90 μL whole blood is added and incubated 20 min at room temperature. 11 μL of 10×LTB4 (final concentration 25 nM for mouse or 10 nM human) is added and incubated at 37° C. for 30 min. The reaction is stopped by incubating the plate on ice for 5 min. The cells are stained with 10 μL anti-mouse or anti-human CD11b-PE (BD Biosciences diluted 1:20 for mouse and undiluted for human) and incubated on ice for 30 min in the dark (for mouse experiments, 10 μL anti-mouse LY6G-FITC antibody (BD Pharmingen) diluted 1:25 is added for the final 10 min) Red blood cells (RBCs) are lysed by adding 1.5 mL of 1×BD FACSlyse (BD Biosciences) and incubating for 10 min at room temperature in the dark. Cells are washed once with 1.5 mL DPBS and then fixed in 400 μL of 1% Cytofix. Mouse neutrophils are isolated by gating strategy LY6G-FITC positive and human neutrophils are isolated by light scatter properties. Data are analyzed with WinList software (Verity Software House) to determine mean and median fluorescent intensity values for CD11b-PE from neutrophil population.

$LTB_4$-induced CD11b expression in neutrophils is inhibited dose-dependently in this preclinical model by the compound of Example 2 and Example 2 blocks $LTB_4$-induced CD 11b expression in mouse and human whole blood neutrophils. $LTB_4$-induced expression of CD11b in human whole blood neutrophils is blocked with an $IC_{50}$ of 193 nM. Similarly, the compound of Example 2 inhibits CD11b expression in mouse whole blood neutrophils with an $IC_{50}$ of 1.45 μM.

Ligand Activated Peroxisome Proliferator-Activated Receptor Alpha, Delta and Gamma (PPAR α, δ, γ) Binding Assay $LTB_4$ and BLT receptor antagonists have been shown to be ligands of the nuclear receptor subfamily of peroxisome proliferator activated receptors (PPAR) and is believed to be a limitation in their development opportunities (Devchand et al *J. Biol. Chem.* (1999), 274: 23341-23348; Devchand et al. *Nature* (1996), 384: 39-43).

PPAR Functional Lysate Preparation:

Generally, these cell lines are generated using commercially available materials and by procedures known to those skilled in the art.

The nucleotide sequences encoding full-length PPARα receptor DNA (National Center for Biotechnology Information (NCBI) Reference Sequence NM_005036.4), PPARδ receptor DNA (NCBI Reference Sequence NM_006238.4), PPARγ receptor DNA (NCBI Reference Sequence NM_015869.4) and Retinoid X Receptor (RXR) α DNA (NCBI Reference Sequence NM_002957.4) are synthesized and inserted into pFastBacHTb (Invitrogen) vector in-framed with the N-terminal HIS tag from the vector. Recombinant bacmid (baculovirus shuttle vector plasmid) are created by transforming DH10Bac cells and isolating DNA from white colonies according to the manufacturer's protocol of Bac-to-Bac Baculovirus Expression system (Invitrogen; See also Invitrogen User Manual, Version F, dated 4 Sep. 2010; and Invitrogen Instruction Manual dated 27 Feb. 2002). Sf9 cells are transfected in 6-well plates at $0.9\times10^6$ cells/well using CellFectin reagent (Invitrogen). P0 virus is collected at 72 h post-transfection and used to infect Sf9 insect cells in suspension at 100 μL of P0 virus per 50 mL cells at $1.5\times10^6$ cells/mL. P1 virus is collected after 96 h. For protein production, 1 L of Sf9 cells are infected at $1.5\times10^6$ cells/mL with 5 mL of P1 virus and the cells harvested after 48 h. To prepare cell lysate, cell pellets from 1 L culture are resuspended with 12.5 mL of ice-cold lysis buffer (20 mM HEPES, pH7.8, 160 mM KCl, 1 mM $MgCl_2$, 2 mM dithiothreitol (DTT), 1% 3-[(3-chloramidopropyl)dimethylammonio]-1-propanesulfonate (CHAPS), 40% glycerol, 1× Roche protease inhibitor cocktail) for PPAR or lysis buffer B (10 mM Tris-HCl, pH7.5, 500 mM NaCl, 1 mM EDTA, 1 mM DTT, 50% Glycerol, 1× Roche protease inhibitor cocktail) for RXRα, and then homogenized and sonicated on ice. After centrifugation on Beckman JA18 rotor at 16,500 rpm for 45 min at 4° C., the supernatant is aliquoted and frozen at −80° C. The protein concentration is determined by Bradford assay using BSA as the standard.

Binding Affinities of Compounds for the PPAR α, δ, γ Receptors are Assessed Using Scintillation Proximity Assay (SPA) Technology.

Biotinylated oligonucleotide(DR2) 5'TAATGTAGG-TAATAGTTCAATAGGTCAAAGGG3' (SEQ ID NO: 1) is used for binding of receptors to Yttrium silicate streptavidin-coated SPA beads (Perkin Elmer). The PPAR α, δ, γ and Retinoid X Receptor (RXR) α receptors (endogenously expressed as heterodimers) are cell lysates from Baculovirus expression systems in Sf9 cells. The DR2 is attached to the Streptavidin SPA beads by mixing over a 30 min period at room temperature in a binding buffer containing 10 mM HEPES at pH 7.8, 80 mM KCl, 0.5 mM $MgCl_2$, 1 mM DTT, 0.5% CHAPS and 16.6 μg bovine serum albumin. The mixture is spun at 2000 rpm for 3 min to pellet the bead-oligo mix. The supernatant is removed and the bead-oligo pellet resuspended in the same binding buffer as above. The cell lysates are incubated in each well with one of 11 concentrations of compound, ranging from 0.17 to 10,000 nM, in the presence of ~0.0338 μCi tritiated GW2331 (racemic 2-[4-[2-[[(2,4-difluorophenyl)carbamoyl](heptyl)amino]ethyl]phenoxy]-2-methylbutanoic acid) for the alpha and delta receptors and ~0.0373 μCi tritiated 2-methyl-2-[4-[3-[propyl[(5-pyridin-2-ylthiophen-2-yl)sulfonyl]amino]propyl]phenoxy]propanoic acid for the gamma receptor, 110.3 μg of SPA Streptavidin coated beads, 0.126 nM HD Oligo DR2, and either 0.3 μg PPARα with 0.5 μg RXRα, 0.5 μg PPARγ with 0.5 μg RXRα, or 1.25 μg PPARγ with 3.03 μg RXRα in the binding buffer above plus 14% glycerol and 5 μg of sheared salmon sperm DNA. Non-specific binding is determined in the presence of 10000 nM unlabeled GW2331 (Kliewer, S. A. et al *Proc. Natl. Acad. Sci. USA* (1997), 94: 4318-4323) for the alpha and delta receptors and 2-methyl-2-[4-[3-[propyl[(5-pyridin-2-ylthiophen-2-yl)sulfonyl]amino]-propyl]phenoxy]propanoic (WO 2004/073606) for the gamma receptor. The binding reaction (100 μL per well in a 96 well [Costar 3632] plate) is incubated for 10 h and counted as disintegrations per minute (dpm) on a Wallac Microbeta Luminometer Liquid Scintillation Counter. Receptor binding affinity ($IC_{50}$) for the compounds is determined by fitting an 11 point concentration-response curve with a 4-paramater logistic equation. $K_i$ is determined from the $IC_{50}$ using the Cheng-Prussoff equation and Kd determined by saturation binding.

Tritiated GW2331 can be obtained by generally following procedures in the literature for synthesis of the gem-dimethyl analogue (WO 92/10468; Hawke, R. L. et al *J. Lipid Res.* 1997, 38:1189-1203) to obtain the non-tritiated material. The tritiation can be accomplished using tritium gas and Crabtree's Catalyst (Heys, J. R. et al *J. Labelled Cpd. Radiopharm.* (1999), 42: 797-807) which places the tritium in the ortho position of the difluorophenyl. Alternatively, tritium can be placed in the heptyl portion of the molecule by palladium catalyzed reduction with tritium gas of the heptenyl analogue (ibid, Kliewer, S. A).

Tritiated 2-methyl-2-[4-[3-[propyl[(5-pyridin-2-ylthiophen-2-yl)sulfonyl]amino]propyl]phenoxy]propanoic acid can be made by catalytic reduction of the ally precursor with tritium gas. The ally precursor (2-[4-[3-[allyl-[[5-(2-pyridyl)-2-thienyl]sulfonyl]amino]propyl]phenoxy]-2-methyl-propanoic acid) can generally be made by following procedures in WO 2004/073606, beginning with ethyl 2-methyl-2-[4-[3-(p-tolylsulfonyloxy)propyl]phenoxy]propanoate in reaction with allylamine, followed by sulfonylation with 5-(2-pyridinyl)-2-thiophenesulfonyl chloride and hydrolysis of the ethyl ester.

Use of the two radioligands can be found in the literature (Burris et al. *Molecular Pharmacology*, 2004 67: 948-954 and Xu et al. *J. Med. Chem.* 2004, 47: 2422-2425).

Following a protocol essentially as described above the compound of Example 2 displayed a $K_i$ in the PPAR α, δ, γ binding assays of about 617 nM (n=3), >8830 nM (n=4), and 1380 nM (n=2) respectively. These data demonstrate that the compound of Example 2 is only weakly interactive, with PPAR receptors. The activity is believed to evidence selectivity and not present a development limitation.

In Vivo Assay Procedures:

CaCl$_2$-Induced AAA Animal Efficacy Model

A targeted application of a calcium chloride solution to the mouse aorta induces vessel dilatation Chiou et al. *J. Surg. Res.* (2001), 99: 371-376; Lomgo et al. *J. Clin. Invest.* (2002), 110: 625-632. Two weeks after treatment, the vessel dilatation compared to the original vessel diameter becomes statistically significant, with up to 75% increase of aortic lumenal perimeter after 4 weeks. Calcium precipitates have been localized primarily within the elastic network of the media. Disruption of this structure by the calcium-elastic tissue complex weakens the vessel wall, contributing to aneurysm formation. This injury also serves as a proinflammatory stimulus, recruiting neutrophils, lymphocytes, monocytes, and mast cells.

Animals:
Mice: 129SvEv males, 7 weeks of age, are acquired from Taconic Farms, Germantown, N.Y., USA.
Rats: Sprague-Dawley rats, 7-8 weeks of age, are acquired from Harlan, Indianapolis, Ind., USA
Aneurysm Induction Model: All procedures are performed in accordance with Eli Lilly and Company Institutional Animal Care and Use guidelines. Upon their arrival, animals have a one week acclimation period during which they have ad libitum access to standard rodent chow (Purina #2014) and house water. Following the acclimation period, animals are anesthetized with isoflurane, and a laparotomy is performed for the CaCl$_2$-stimulated induction of the abdominal aortic aneurysm (AAA). The abdominal aorta from the level of the renal arteries to the iliac bifurcation is isolated from the inferior vena cava and surrounding connective tissues using microsurgical techniques. Once isolated, the region of interest (ROI) of the abdominal aorta is wrapped with sterile, cotton gauze presoaked in a 0.25 M CaCl$_2$ solution. In sham control animals, 0.9% saline is substituted for CaCl$_2$. After 7 min, the gauze is removed and a second CaCl$_2$ soaked gauze reapplied. Following the second 7 min period, the gauze is removed, the aorta rinsed with 0.9% saline and the abdomen closed Animals are returned to general housing at the end of their surgical day.

Compound Administration: Mice receive test compound (Example 2) by oral gavage at a dose volume of 10 mL/kg of body weight, and rats receive test compound (Example 2) by oral gavage at a dose volume of 2.5 mL/kg of body weight. Compound administration is BID (a.m. and p.m.) with the first dose given one day prior to surgery (p.m.) and the second dose given the morning of surgery. Animals do not receive a p.m. dose on the day of surgery. The day after surgery, dosing continues BID for 28 days.

Aortic Measurements by Ultrasound: Twenty-eight days following surgery, animals are anesthetized and undergo abdominal ultrasound measurements using the eSaote MyLab 30 Gold Biosound Ultrasound unit equipped with a 7.5 MHz probe. Due to the asymmetrical development of AAA in preclinical CaCl$_2$ rodent models, arterial measurements are taken of outside diameter and lumenal (inside) diameter during peak systole along both the longitudinal and cross sectional axes to identify the most dilated section within the ROI. Interior cross sectional lumenal perimeter measurements (mm) are collected at that point to assess efficacy and statistically analyzed with JMP® 7 software (Cary, N.C.).

Statistical Analysis: Measurements of lumenal perimeter are expressed as mean values±SE. To determine the percent of AAA inhibition for the drug treated groups, the measurements from the vehicle-treated sham control group represent 100% inhibition of AAA development, while the measurements from the vehicle treated CaCl$_2$ group represent 0% inhibition of AAA development. Statistical analysis is performed with JMP® 7 software (Cary, N.C.) and Dunnett's Test is used for statistical comparisons across treatment groups. Statistical significance is accepted at P<0.05.

The efficacy signal window in the CaCl$_2$-induced abdominal aortic aneurysm model is determined by the lumenal perimeter of the aorta in mice treated with saline-soaked gauze followed by 4-weeks dosing with vehicle that determines 100% efficacy ("Sham Vehicle") and the lumenal perimeter of the aorta in mice treated with CaCl$_2$-soaked gauze followed by 4-weeks dosing with vehicle ("Vehicle") that determines 0% efficacy.

Following a protocol essentially as described above, using 129SvEv mice, the luminenal perimeter of the aorta is statistically reduced (Table 1), as compared to Vehicle-treated mice, using the compound of Example 2, and evidences the compound of Example 2 reduces AAA in this animal model.

TABLE 1

In Vivo Percentage (%) Reduction of AAA in mice

| Group | % Reduced (±S.E.) | P Value |
|---|---|---|
| Vehicle | 0% ± 9 | |
| 10 mg/kg b.i.d. | 41% ± 13 | p = 0.0522 |
| 30 mg/kg b.i.d. | 48% ± 10 | p = 0.0179 |
| 60 mg/kg b.i.d. | 58% ± 13 | p = 0.0028 |
| Sham | 100% ± 8 | p = <0.0001 |

In a similar study design, the ability of the compound of Example 2 to modulate aortic aneurysm dilation following $CaCl_2$-induced injury is evaluated in Sprague-Dawley rats. The lumenal perimeter of the aorta is statistically reduced, as compared to Vehicle-treated rats (Table 2), and evidences that the compound of Example 2 reduces AAA.

TABLE 2

In Vivo Percentage (%) Reduction of AAA in rats

| Group | % Reduced (±S.E.) | P Value |
|---|---|---|
| Vehicle | 0% ± 7 | |
| 3 mg/kg b.i.d. | 46% ± 7 | p = 0.0001 |
| 10 mg/kg b.i.d. | 69% ± 4 | p = <0.0001 |
| 30 mg/kg b.i.d. | 85% ± 5 | p = <0.0001 |
| 60 mg/kg b.i.d. | 69% ± 10 | p = <0.0001 |
| Sham | 100% ± 6 | p = <0.0001 |

LDLr KO Mouse Brachiocephalic Arch Atherosclerosis Model

The compound of Example 2 is tested in the low density lipoprotein (LDL) receptor knock-out (LDLr KO) mouse model of atherosclerosis. Mice deficient in the ability to encode and synthesize the LDL receptor (LDLr KO) are hypercholesterolemic, especially when maintained on high cholesterol diet, Ishibashi et al. *J. Clin. Invest.* (1994), 93: 1885-1893. In the large arteries, LDLr KO mice develop spontaneous atherosclerotic lesions that mimic major features of the cellular, lipid, and extracellular matrix composition of human lesions. An important constituent of both human and mouse lesions is the lipid-laden macrophage or "foam cell" in the arterial subendothelium. The esterified cholesterol stored by macrophages is a surrogate for lesion development. Assay of esterified cholesterol directly from mouse arterial tissue (by LC/MS) provides a rapid index of lesion burden. The LDLr KO model used in the present study takes advantage of the rapid development of mature atherosclerotic plaques in the brachiocephalic artery (BCA). Primary endpoints for the study are arterial cholesteryl ester content and lesion dimensions obtained by light microscopic measurement of lesions in serial cross-sections of the artery.

LDLr KO mice (JAX #002207), 7 week old males, were obtained from The Jackson Laboratory (Bar Harbor, Me.). Upon arrival at the testing facility and continuing for a total of 10 weeks, mice were housed individually and fed the atherogenic diet TD.88137 (Teklad) ad libitum. During the first 6 weeks, the mice rested undisturbed in their cages. During the last 4 weeks, the mice received the test compound twice daily by oral gavage. Data from the evaluations are reported in Table 3, below.

TABLE 3

LDLr KO mouse BCA atherosclerosis lesion area illustrates dose-dependent reduction in atherosclerosis endpoints. Comparisons between treatment groups were made with a 1-way ANOVA followed by Dunnett's test.

| | vehicle | 3 mg/kg BID Example 2 | 10 mg/kg BID Example 2 | 30 mg/kg BID Example 2 |
|---|---|---|---|---|
| Lesion area (mm²) | 50,686 | 23,737 | 21,247 | 17,090 |
| Lesion area vs. vehicle | | −53%* (p < 0.049) | −58%* (p < 0.034) | −66%* (p < 0.017) |
| Cholesteryl ester (nmoles) | 22.50 | 17.95 | 16.97 | 14.51 |
| Cholesteryl ester vs. vehicle | | −8% (p = NS) | −18% (p < 0.09) | −23%* (p < 0.04) |
| Macrophage area (brown color, mm²) | 18,571 | 6,515 | 2,864 | 8,520 |
| Macrophage area vs. vehicle | | −65%* (p < 0.02) | −84%* (p < 0.002) | −54% (p < 0.09) |
| AUC (ng · hr/ml) | | 1,106 | 5,375 | 12,849 |

Table 3 shows that the compound of Example 2 at 30 mg/kg b.i.d dosing reduced BCA cholesteryl ester (CE) content 23% compared to the vehicle treated group (p<0.04). The compound of Example 2 at 10 mg/kg b.i.d, although less effective than at 30 mg/kg b.i.d., reduced CE content by 18% compared to vehicle treatment (p<0.09). The trend toward a significant reduction of BCA atherosclerosis suggested by these surrogate data is confirmed and extended by the direct measurement of BCA lesions. Table 3 shows a significant reduction in lesion area produced by the compound of Example 2 at 30 mg/kg oral b.i.d dosing. Treatment at this dose results in a reduction of lesion area of 66% compared to treatment with vehicle alone (p<0.017). The 58% and 53% reduction in lesion area produced by the compound of Example 2 at 10 mg/kg b.i.d and 3 mg/kg b.i.d. dosing, respectively, illustrates a similar dose-response effect as compared to the effect on BCA CE content.

---

---

I claim:

1. A compound of Formula (I)

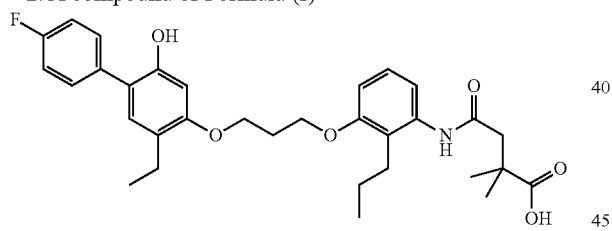

or a pharmaceutically acceptable salt thereof.

2. A compound of claim 1 which is Sodium 4-[[3-[3-[2-ethyl-4-(4-fluorophenyl)-5-hydroxy-phenoxy]propoxy]-2-propyl-phenyl]amino]-2,2-dimethyl-4-oxo-butanoate.

3. A pharmaceutical composition comprising a compound according to claim 2 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,187,411 B2 | Page 1 of 1 |
| APPLICATION NO. | : 14/359924 | |
| DATED | : November 17, 2015 | |
| INVENTOR(S) | : Douglas Richard Stack | |

It is certified that error appears in the above-identified patent and that said Letters Patent is hereby corrected as shown below:

At Title Page Column 1, item (56) (Other Publications) Line 2: Delete "[3-2-ethyl-" and insert -- "[3-[2-ethyl- --, therefor.

Signed and Sealed this
Seventeenth Day of May, 2016

Michelle K. Lee
*Director of the United States Patent and Trademark Office*